United States Patent [19]

Smith et al.

[11] Patent Number: 5,373,844
[45] Date of Patent: Dec. 20, 1994

[54] INVERSE TREATMENT PLANNING METHOD AND APPARATUS FOR STEREOTACTIC RADIOSURGERY

[75] Inventors: Vernon Smith, San Rafael; Randall A. Stone, San Francisco, both of Calif.

[73] Assignee: The Regents of the University of California, Oakland, Calif.

[21] Appl. No.: 76,740

[22] Filed: Jun. 14, 1993

[51] Int. Cl.⁵ .................................. A61B 6/00
[52] U.S. Cl. ............................ 128/653.1; 364/413.26; 606/130; 378/65
[58] Field of Search ............... 128/653.1, 653.2, 659; 606/130; 378/65; 364/413.13, 413.14, 413.26

[56] References Cited
U.S. PATENT DOCUMENTS

| | | |
|---|---|---|
| 3,011,700 | 12/1961 | Barnard et al. . |
| 3,871,579 | 3/1975 | Inamura . |
| 3,987,281 | 10/1976 | Hodes ........................ 364/413.26 |
| 4,172,979 | 10/1979 | Morrison ........................ 378/65 |
| 4,455,609 | 6/1984 | Inamura et al. . |
| 4,729,099 | 3/1988 | Iverson et al. . |
| 4,869,247 | 9/1989 | Howard, III et al. . |
| 5,008,907 | 4/1991 | Norman et al. . |
| 5,027,818 | 7/1991 | Bova et al. . |
| 5,037,374 | 8/1991 | Carol . |
| 5,107,839 | 4/1992 | Houdek et al. . |
| 5,205,289 | 4/1993 | Hardy et al. . |
| 5,207,223 | 5/1993 | Alder . |
| 5,211,164 | 5/1993 | Allen . |

*Primary Examiner*—Ruth S. Smith
*Attorney, Agent, or Firm*—John P. O'Banion

[57] ABSTRACT

An apparatus and method for inverse treatment planning for stereotactic radiosurgery is disclosed. Target position and volume are initially determined by establishing a reliable x,y,z coordinate system using a stereotactic frame and imaging the regions of interest in the patient. The target volume is geometrically packed with "shot volumes" determined by isodose curves of single Leksell "gamma knife" shots on a series of two-dimensional slices to generate a net treatment volume. A final treatment plan is generated by further packing the target volume with the treatment volume determined by the isodose surface of all of the gamma knife shots. Once the final treatment plan is developed, the patient is treated with the "gamma knife." The result is that the target volume is sufficiently irradiated while the amount of radiation to surrounding tissue or critical structures in the patient is minimized.

14 Claims, 6 Drawing Sheets

INVERSE TREATMENT PLANNING METHOD AND APPARATUS FOR STEREOTACTIC RADIOSURGERY

GOVERNMENT SUPPORT

This invention was made with Government support under Grant Nos. NCI-CA-09215-12 and CA-09215-13 awarded by the National Institute of Health. The Government has certain rights in this invention.

BACKGROUND OF THE INVENTION

1. Field of the Invention

This invention pertains generally to treatment of a patient by stereotactic radiosurgery, and more particularly to optimizing dose delivery through inverse treatment planning.

2. Description of the Background Art

Stereotactic radiosurgery is a well-known treatment option available to an oncologist. The procedure can be carried out using a Leksell gamma unit (LGU) commonly referred to as a "Gamma Knife" (marketed by Elekta Corporation, Stockholm, Sweden), a linear accelerator, or similar apparatus. In treating a patient with such an apparatus, the goal of the oncologist is to deliver one or more "doses" so as to maximize irradiation of a target volume of diseased tissue while minimizing irradiation of surrounding healthy tissue. This requires careful and well defined planning prior to treating the patient.

Currently, radiosurgical treatment planning is performed in an iterative manner where the planner uses experience to "guess" at a plan to treat a given target volume. The planner chooses how many "shots" or isocenters to use, as well as the location in three dimensions, the collimator size, and the weighting to be used for each isocenter. A treatment planning computer calculates the dose distribution resulting from this guess, and the efficacy of the plan is evaluated by comparing the resulting isodose lines with the target volume as delineated by contour lines drawn on a series of planar CT (computed tomography) or MRI (magnetic resonance imaging) slices. The planner attempts to improve the plan by moving isocenters, changing weights, and so forth, so that the calculated isodose lines give a better match to the target contours. Eventually, after several iterations, the plan is judged to match the target, or is accepted as the best practical match in consideration of the time constraints imposed on the number of iterations that can be tried.

Various approaches to computerized treatment planning have been developed to assist the planner in his or her optimization of dose patterns. However, when the target volume is large and has a complicated shape, it is very difficult for a human planner to produce a good plan in a reasonable time, even with the assistance of a computer.

The present invention is directed to "inverse" treatment planning. Prior to the present invention, however, inverse treatment planning for radiosurgery performed with an apparatus such as a Leksell Gamma Knife has not been practical. For example, methods which use an unconstrained optimization tend to use many shots of the smallest aperture size. Such an approach is not practical, especially with large volumes, because the time required to treat a given target volume with a very large number of shots is prohibitive. We have discovered that the number of shots generally should not exceed fifteen, and that using a smaller number of shots with larger aperture sizes can often produce almost as satisfactory a plan. We have further discovered that, if optimization based on isodose line matching of the target contour is initiated without first generating an approximate estimate of number of shots and location, then long computation times will be involved.

Therefore, there is a need for an apparatus and method for optimizing radiosurgical dose delivery and shape which is accurate and efficient. The present invention satisfies those, as well as other needs, and overcomes the deficiencies in prior methods and devices.

SUMMARY OF THE INVENTION

This invention pertains generally to an apparatus and method for "inverse" treatment planning for stereotactic radiosurgery of a patient. In general terms, the method of the present invention starts with a defined target position and volume within the patient to be treated, and utilizes a treatment computer to produce a treatment plan that fits the target volume. This method saves time, and is more thorough than a human or prior computerized techniques in its search for an optimal treatment plan. In addition to independently producing an optimal plan, the method can be employed as a tool for iteratively optimizing selected shots or quantities.

By way of example and not of limitation, the target position and volume are initially determined by establishing a reliable x,y,z coordinate system using a stereotactic frame or the like, and imaging the regions of interest in the patient using an imaging system such as computed tomography (CT), magnetic resonance imaging (MRI), angiography or the like. Next, the target volume is geometrically packed with individual "shot volumes" from a Leksell Gamma Knife or the like to produce a treament volume (i.e., the volume defined by a specific isodose surface of the total dose distribution resulting from all the LGU shots, commonly the 50% isodose surface). This step is followed by a conformation packing of the treatment volume to the target volume.

An approximate solution is generated by the geometric packing step which optimizes the packing of shot volumes determined by the isodose curves of single LGU shots on a series of two-dimensional slices. This process will be referred to as "geometric packing." A final treatment plan is generated by the conformation packing step which optimizes the packing of the treatment volume determined by the isodose surface of all of the LGU shots, to the volume. This is done by matching the treatment volume (represented by isodose contours on the slices) with the target volume as determined by the target contours on the image slices. This process will be referred to as "conformation packing." The two steps are similar in implementation as the geometric packing can be thought of as a conformation of the union of the shot volume to the target volume.

Once the treatment plan is developed, the patient is treated with the result that the target volume is sufficiently irradiated while the amount of radiation to surrounding tissue or critical structures in the patient is minimized.

Use of the present invention requires a definition of the patient geometry and desired isodose curve upon which to optimize. The patient geometry is defined by specifying the target and critical structures on a series of contours on the slice set of images. Once the target and critical structures are defined, the approximate solution can be obtained by geometrically packing the target volume with shot volumes. Using the approximate solution to generate the dose distribution, the isodose surface chosen to optimize upon can now be found. Modification of the treatment volume, specified by the given isodose value, by optimizing the parameters, then produces the optimal plan. The isodose contours generated by the optimal plan can be directly compared to the target and critical structure contours to ascertain the quality and acceptability of the plan (this can be done automatically). If the plan is found to be acceptable, the shot configuration can be used to calculate the Gamma Knife shot treatment times on a FDA approved planning program.

An object of the invention is to develop an optimal treatment plan for stereotactic radiosurgery.

Another object of the invention is to match radiosurgical doses to the contour of a target.

Another object of the invention is to match radiosurgical doses to the volume of a target.

Another object of the invention is to effectively treat a target volume without damaging adjacent tissue or critical structures.

Another object of the invention is to optimize the placement of dosages from a radiosurgical apparatus.

Another object of the invention is to produce an optimal stereotactic radiosurgical plan in a reasonable amount of time with a limited number of shots.

Another object of the invention is to provide for inverse treatment planning for stereotactic radiosurgery.

Further objects and advantages of the invention will be brought out in the following portions of the specification, wherein the detailed description is for the purpose of fully disclosing preferred embodiments of the invention without placing limitations thereon.

BRIEF DESCRIPTION OF THE DRAWINGS

The invention will be more fully understood by reference to the following drawings which are for illustrative purposes only.

DESCRIPTION OF THE PREFERRED EMBODIMENTS

Figure 3A:
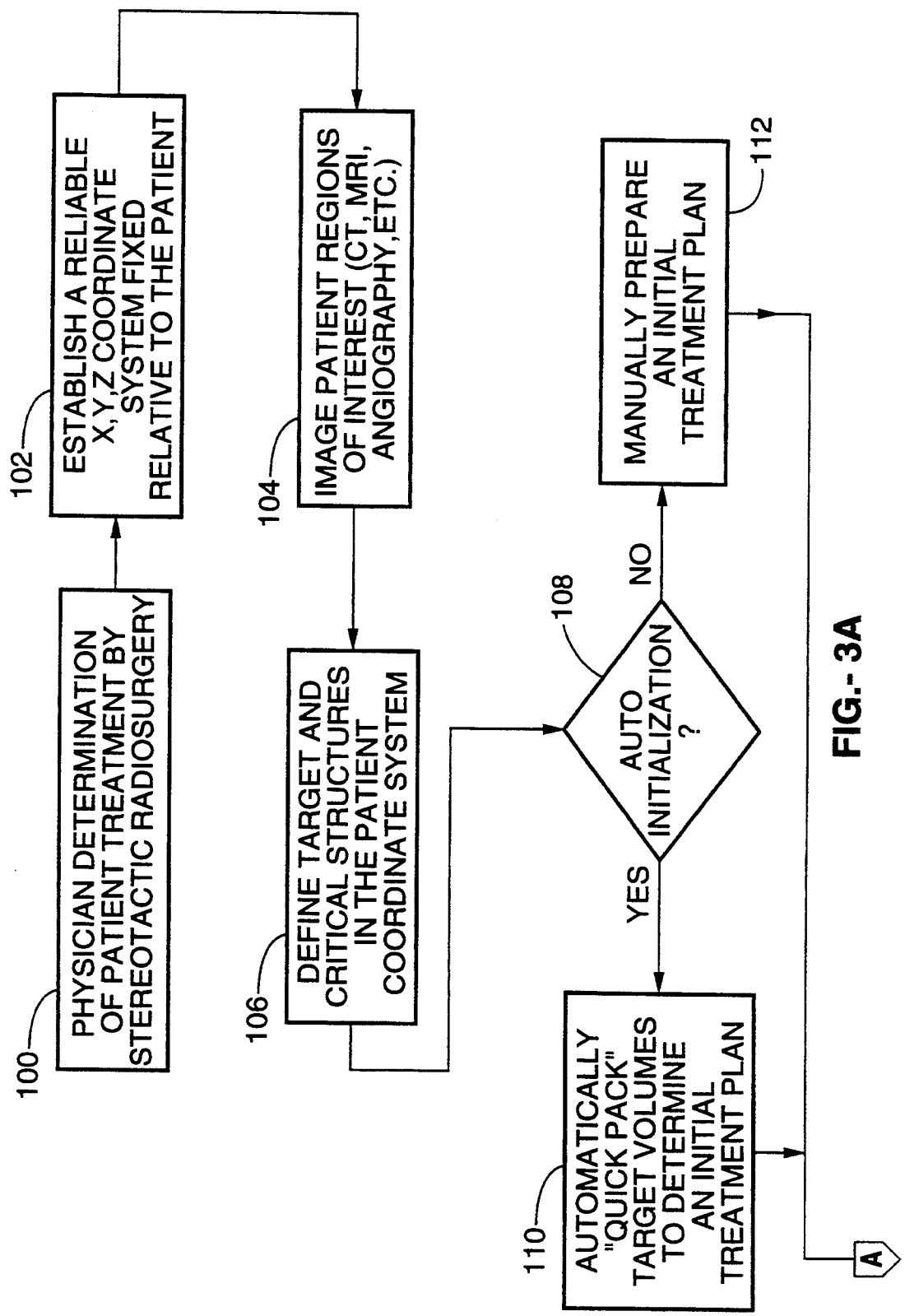
FIG. 3A through FIG. 3C is a process flow diagram in accordance with present invention.
Figure 3B:
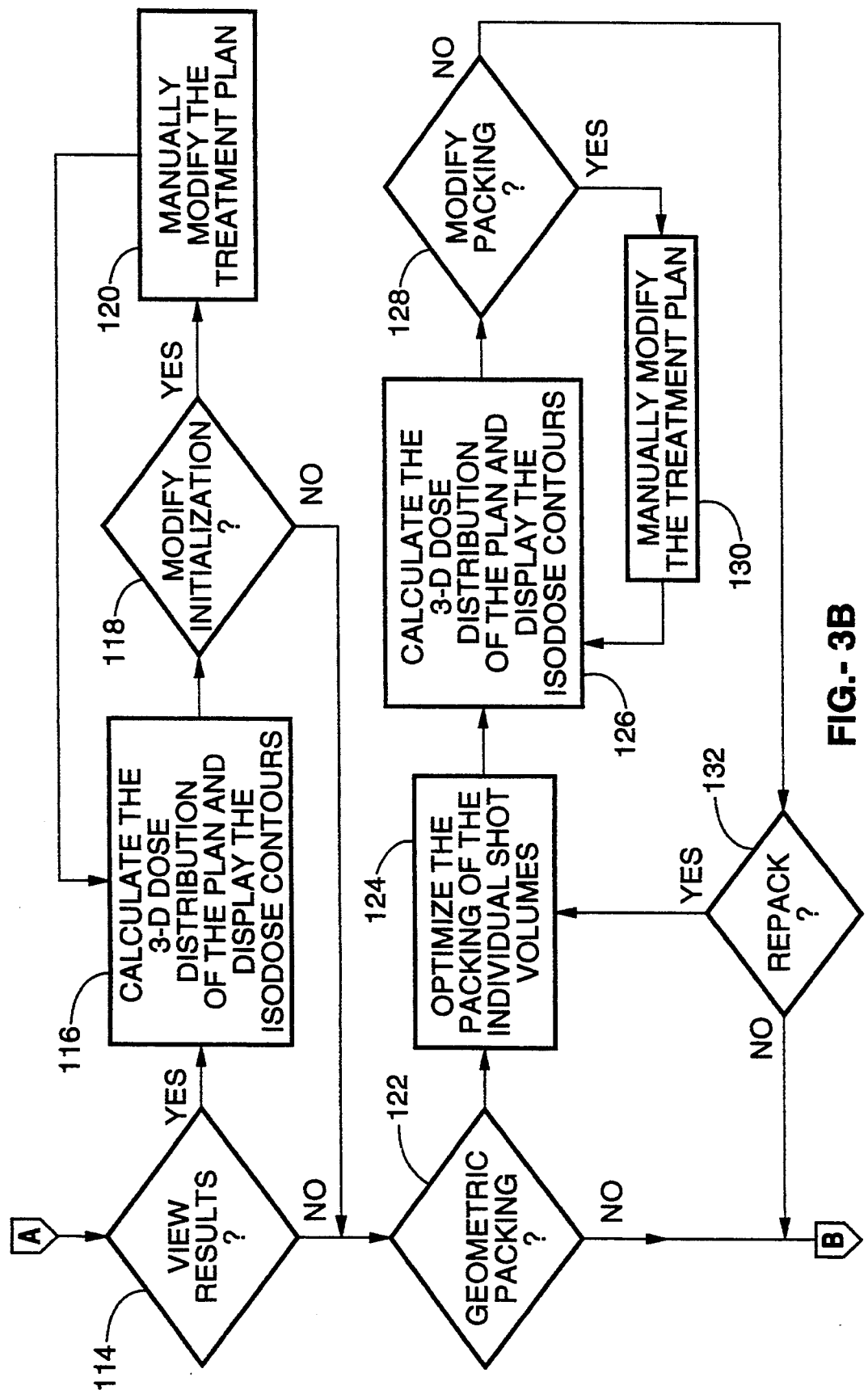
Figure 3C:
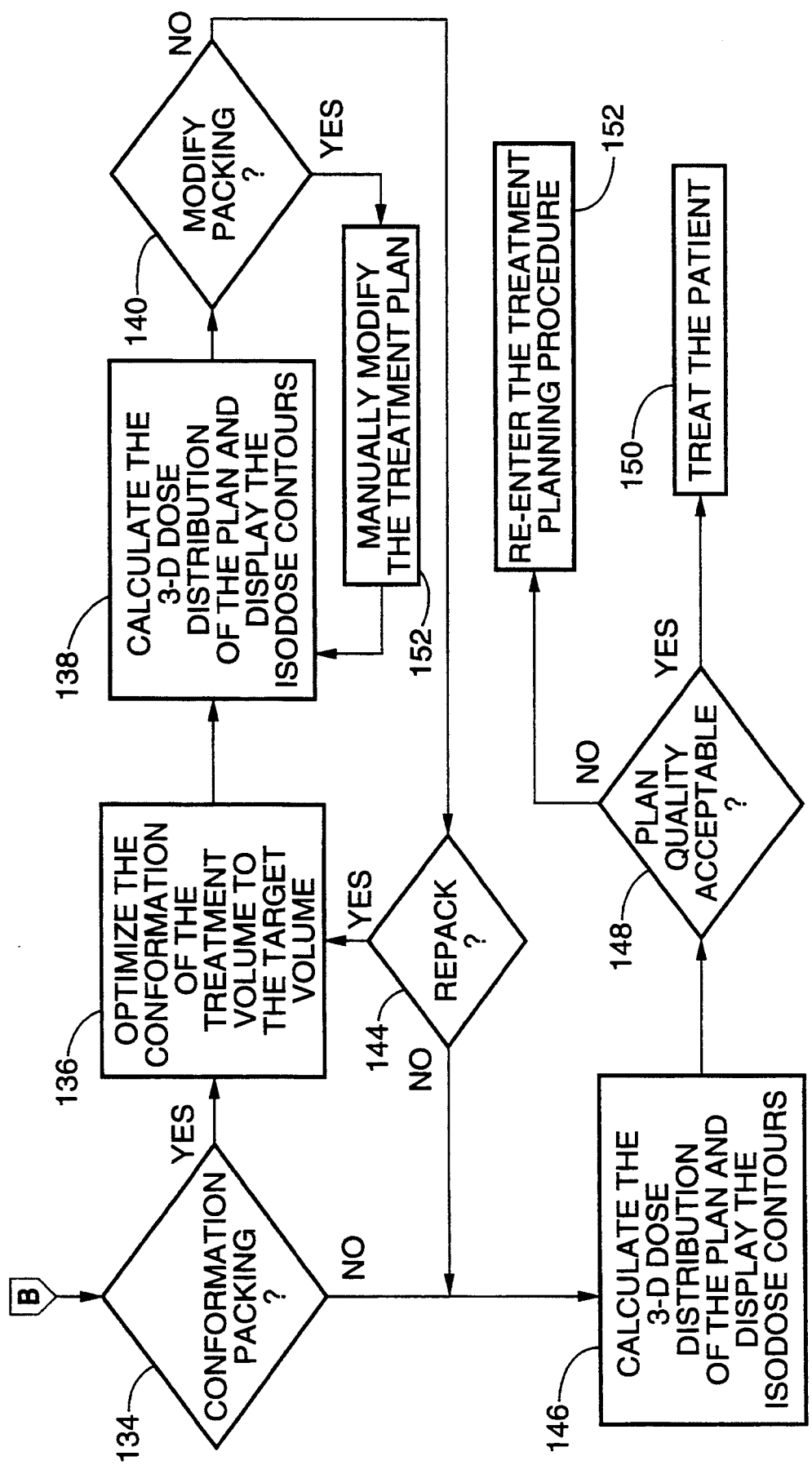
Figure 4:
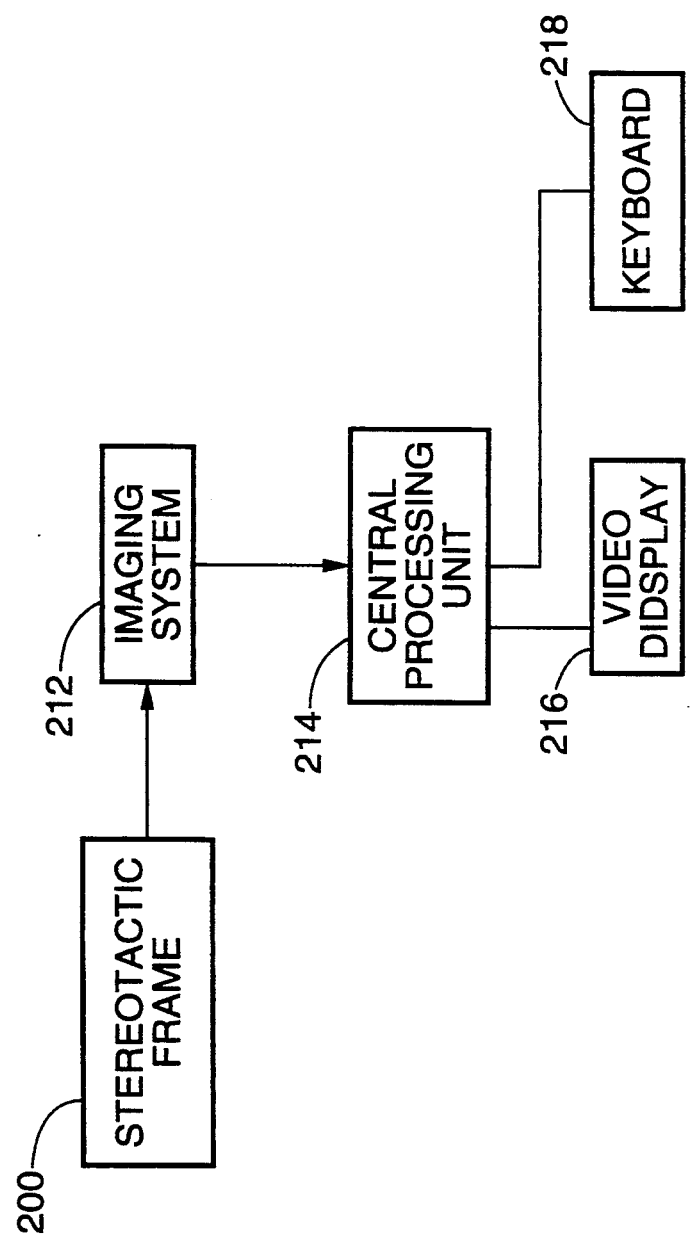
FIG. 4 is a system block diagram in accordance with the present invention.

Referring more specifically to the drawings, for illustrative purposes the present invention is embodied in the method generally shown in FIG. 3A through FIG. 3C, and the apparatus generally shown in FIG. 4. It will be appreciated that the method may vary as to the details of the steps and their sequence, and that the apparatus may vary as to configuration and details of the parts, without departing from the basic concepts as disclosed herein.

In general terms, the present invention provides for treatment plan optimization by conforming the treatment volume (the volume enclosed by a specific isodose surface) to the defined target volume as closely as possible without exposing critical structures to risk. This is achieved through a geometric packing followed by a conformation packing. In the geometric packing, the optimization involves conforming the union of the individual shot volumes (fixed in shape and size, but not in position or gamma angle) to the target volume. In the conformation packing, the optimization involves conforming the treatment volume (not fixed in shape) to the target volume. In both steps, the intersection of volumes is used to determine the degree or quality of the conformation.

Figure 1:
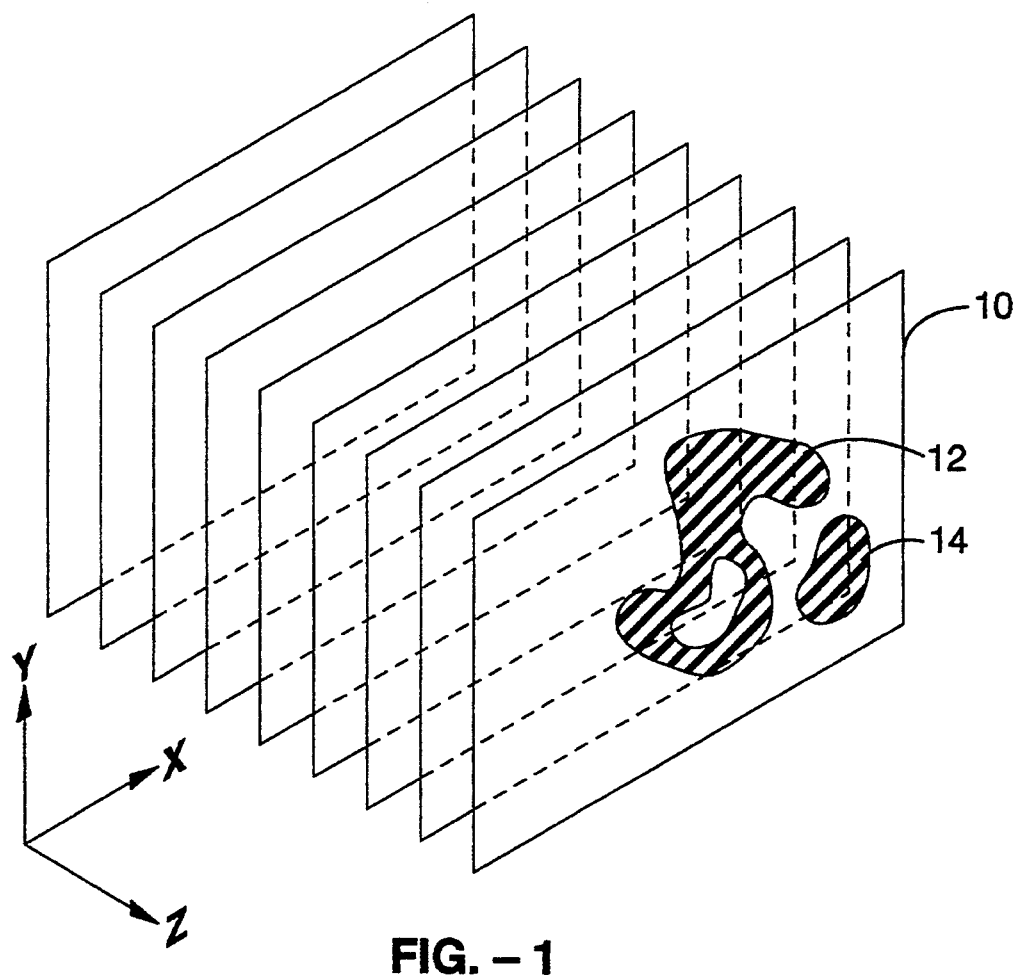
FIG. 1 is a diagrammatic view of a sample target volume represented as a series of planar slices.

Referring to FIG. 1, the target, critical, shot, and treatment volumes are defined or represented by contours on a series of slices 10. In FIG. 1, a plurality of target structure contours 12, 14 can be seen. It should be noted that contours for a particular tissue or other structure can be nested so as to provide multiple crossings (e.g., a long thin snake-like structure twisting in and out of a slice several times) and surface dimples (represented as a hole in a slice through the dimple). Each slice 10, while planar, has a thickness and, thus, represents a slice of volume. Target and critical structures are defined by examination of studies of computed tomography (CT), magnetic resonance imaging (MRI), angiography or similar images from an imaging system prior to initiation of the optimization procedure and are not altered once optimization starts. Shot and treatment volumes are derived from three-dimensional dose calculations and are altered during optimization.

For purposes of geometric packing, the individual shot volumes (one for each aperture size) can be specified a priori by examining the three-dimensional dose data for the shots placed near the target region. The isodose surface used to define the volume of a single shot is that which results in the best conformation of the union of two individual shot volumes lying adjacent to each other and the isodose surface of interest calculated from the three-dimensional dose distribution from both shots. The assumption that the shape of the shot volume is not altered significantly is reasonable for shot translations which are small compared to the distance of the shot isocenters to the outer surface of the patient. For the Leksell Gamma Knife, the shot volumes or shapes can be approximated by ellipsoids. The longest and shortest axes of the ellipsoids typically do not vary by more than about twenty percent. The further approximation of the ellipsoid by a sphere of an LGU standard size (i.e., 4, 8, 14 or 18 mm diameters) is acceptable provided that some error is allowable or that the geometric packing is used only to initialize the conformation packing. (The effect of this error is difficult to predict. However, the effect is expected to be most pronounced at shot boundaries along the axis of symmetry of the many radiation beams of the Gamma Knife). The shot position, gamma angle, and shot volume (i.e., shape) determine the shot contours on the slice set (i.e., the intersection of the shot volume surface with the slices). Using ellipsoidal volumes, all shot contours are ellipses. The ellipses, like the target and critical structure contours, are represented by polygons. Any time a shot (position, gamma angle, or size) is altered in the geometric packing, the corresponding shot contours must be updated.

In the conformation packing, the treatment volume contours is this text (called either shot or dose contours) replace the shot contours used in geometric packing. The contours of the treatment volume are found on each slice by using a two-dimensional contouring routine on a two-dimensional grid of doses in the slice. The two-dimensional dose grid is found using the three-dimensional dose data and interpolation, if required. Any time the shot set (positions, gamma angles, sizes, or weightings) is altered, the treatment volume contours must be updated to reflect the alteration.

Figure 2:
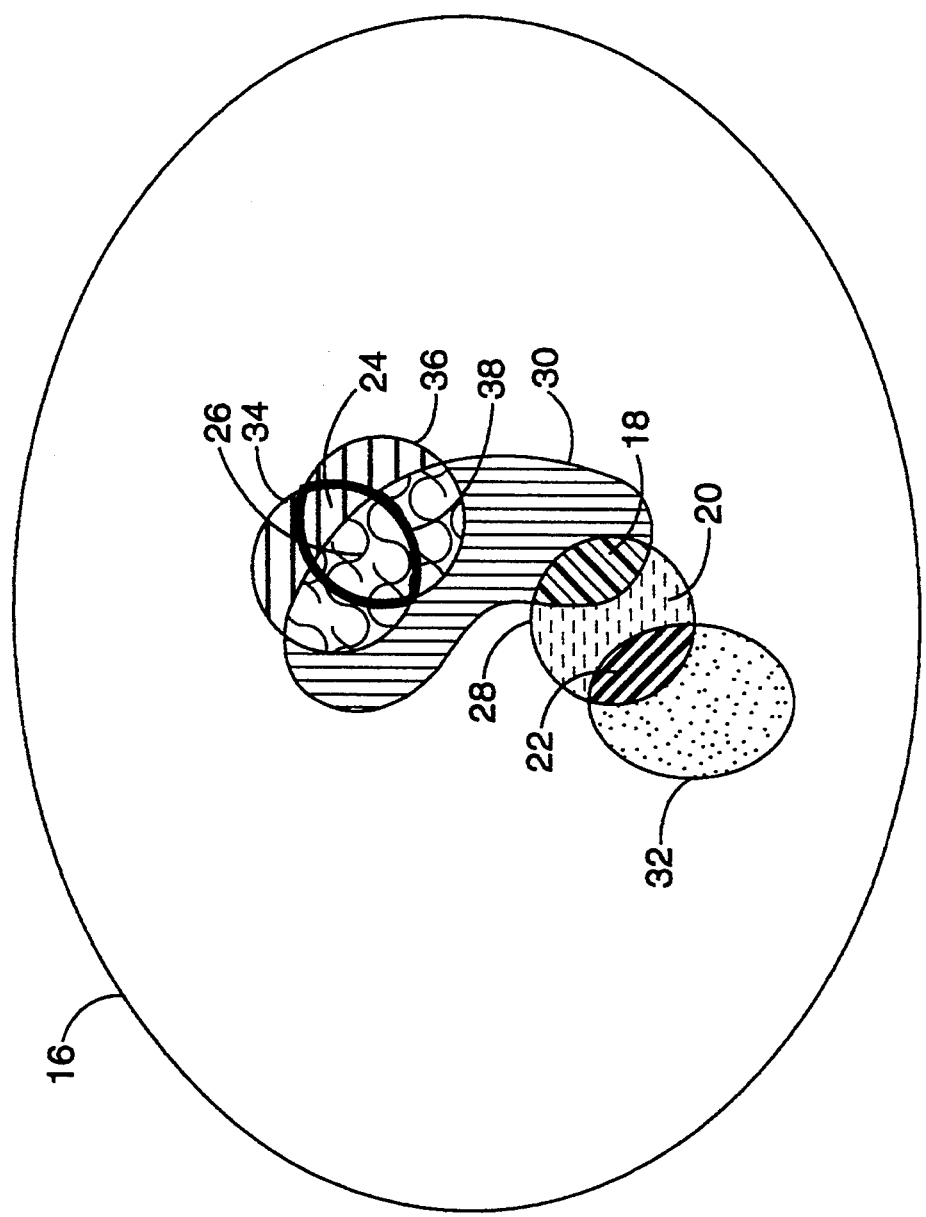
FIG. 2 is a diagrammatic view of a sample slice depicting the contours and overlaps of typical shots, target tissue areas, normal tissue areas, and critical tissue areas.

Referring to FIG. 2, which shows a patient outer contour 16 circumscribing normal, target and critical tissue areas or contours, the contours on each slice are used to calculate area overlaps. The area overlaps translate to volume overlaps when summed over the entire slice set. The four types of area overlaps used in determining the quality of the packing are shot-target overlap 18, shot-normal overlap 20, shot-critical overlap 22, and shot-shot overlap 38. The shot-target overlap 18 is the intersection of the areas inscribed by a specific shot contour 28 and a specific target structure contour 30. The shot-normal overlap 20 is the area of a specific shot contour 28 which lies within normal tissue (i.e., the area within the shot contour 28 which lies outside all target and critical structure contours). The shot-critical overlap 22 is the intersection of the areas inscribed by a specific shot contour 28 and a specific critical structure contour 32. Note that treatment volume contours are not depicted in FIG. 2. The concepts of shot-target, shot-normal, and shot-critical overlaps apply to conformation packing provided that "shot" contour is understood to refer to a treatment volume contour. Treatment volume contours do not overlap so that "shot-shot" overlap does not exist in conformation packing.

Still referring to FIG. 2, when geometrically packing the volume, the shot-shot overlap 38 is the area inscribed by the overlap of two shot contours 34, 36. A shot-shot overlap can, in general, overlap normal, target, and critical areas at the same time. Shot-shot overlap can also overlap with other shot contours but, since that results in an inefficient treatment via excessive shot-shot overlap, shot-shot-shot overlap is already indirectly penalized in the method of the present invention and can be ignored. The contour of the shot-shot overlap is used to calculate the shot-shot overlap of a pair of shots with target and critical structures. In FIG. 2, the shot-shot overlap 38 produces shot-shot-normal overlap 24 and shot-shot-target overlap 26. These shot-shot-target and shot-shot-critical overlaps are required to calculate the total overlap of more than one shot on a target or critical structure, respectively, because the shot-target or shot-critical areas of two different shots can overlap. In the conformation packing, where the treatment volume is used to determine the isodose contours, shot-shot overlap becomes irrelevant because the true isodose contours of the net three-dimensional dose distribution do not overlap.

An optimization function that represents the quality of the packing can be constructed using the four overlaps defined. The function is constructed so that its minimization produces the optimal plan. The object of treatment plan optimization is to conform the treatment volume (the volume enclosed by a specific isodose surface—typically the 50% isodose surface for Gamma Knife treatments) to the defined target volumes(s) as well as possible without exposing critical structures to risk. In the geometric packing step, the optimization translates to conforming the union of the individual shot volumes (each of which is fixed in shape and size, but not to position or gamma angle) to the target volume. In the conformation packing step, the optimization involves conforming the treatment volume (not fixed in shape) to the target volume. In terms of area overlaps, shot-target overlap is desirable and should be maximized in both geometric and conformation packing (thus minimize the negative of this overlap). However, shot-normal and shot-critical overlaps are not desirable and should be minimized. In addition, the uniformity of shot-normal overlaps is important. If the shot-normal overlap is not uniform, one or more shots can extend significantly into the normal tissue, creating a bulge of the treatment volume into normal tissue. A non-linear dependence (i.e., square, cube, exponential, etc.) on shot-normal overlap will produce uniform shot-normal overlaps. Alternatively, the maximum extent of the shot contour from the target contour can be minimized to produce uniformity.

When geometrically packing shot volumes, shot-shot overlap is not desirable and should be minimized. If the shots do not overlap and are packed, the isodose surface of the shots, pair-wise, closely match the union of the shot volumes. However, there are several crucial factors that must be included in the optimization function besides the requirement that shot-shot overlap be minimized if minimization of the optimization function is to be equivalent to production of the optimal treatment plan. The validity of using shot volumes to model the treatment volume has been found to be adversely affected by the formation of hot spots (i.e., a point whose dose is significantly higher than elsewhere in the treatment volume) in regions closely surrounded by several shots or between two shots with a significantly large overlap in comparison with the overlap between other shots. The three-dimensional dose distribution is normalized to the point of maximum dose. The formation of a hot spot results in a shift of the actual isodose surface inward toward the hot spot. This shift is away from the union of the individual shot volumes and can invalidate the use of shot volumes to approximate the treatment volume. To prevent an excessive overlap between any one shot pair, the uniformity of the shot-shot overlaps should be maximized. A non-linear dependence (i.e., square, cube, exponential, etc.) on shot-shot overlap will produce uniform shot-shot overlaps. A more complicated problem is the formation of hot spots between a tight cluster of three or more shots, even if shot-shot overlap is uniform (the shot volumes were designed by comparing the isodose surface of a pair of shots to the individual shot volumes, not clusters to individual shot volumes). A term is required that detects and penalizes the tight cluster formation of three or more shots. This term cannot be easily or reliably be constructed from the shot-shot overlap already defined because a tight cluster can form without a triple of shots all overlapping (i.e., shot-shot-shot overlap) or all shots pair-wise overlapping (i.e., shot-shot overlap between each of the three pairs of shots). A means of detecting tight clusters is to compare the distances between the isocenters of the shots to that produced by shot volume contact. The contact distance depends on the relative position and shape of the shots (both are approximately ellipsoidal). If any triple of shots is found to be pair-wise close (all three pairs), but not necessarily pair-wise overlapping, a contribution can be added to the optimization function, either discouraging the formation of the cluster or encouraging its dissolution. The comparison of the isocenter separation of a pair of shots to the contact distance can also be used to penalize shot-shot overlap rather than using the shot-shot overlaps.

More specifically, for both geometric packing and conformation packing the total optimization function, OPT, is constructed slice by slice as a sum of slice optimization functions, $OPT_s$. The slice optimization functions are constructed primarily on the concept of area overlaps and, therefore, $OPT_s$ can be referred to as the "area optimization function." In calculating the total optimization function OPT, each slice is weighted by the slice thickness. Therefore, the total optimization function OPT represents optimization on volume and can be referred to as the "volume optimization function." This relationship can be seen from the following equation:

$$OPT = \sum_s \Delta_s OPT_s$$

where,
OPT≡volume optimization function;
s≡an index representing a specific slice;
$\Delta_s$≡thickness of slice s; and
$OPT_s$≡area optimization function calculated on slice s.

A weighting factor can also be included in the sum to specify a relative importance of area optimization between slices other than that determined by slice thickness, if desired.

The calculation of the area optimization function in both geometric packing and conformation packing depends on shot-target, shot-normal, and shot-critical area overlaps. These overlaps will be referred to as $ST_s$, $SN_s$, and $SC_s$, respectively. The area optimization also includes a term to penalize the non-uniformity of shot-normal overlaps. This term is referred to as $SNU_s$. Additional terms are added when geometrically packing to compensate, partially, for using individual shot volumes rather than the true isodose surface. The shot-shot overlap and the term used to penalize the non-uniformity of shot-shot overlaps are called $SS_s$ and $SSU_s$, respectively. The term $REP_s$ is added to prevent the tight packing of clusters of several shots. This term creates a repulsion between three or more shots when they are all close together.

For geometric packing, the area optimization function $OPT_s$ is defined as the following equation:

$$OPT_s = -ST_s + SN_s + SC_s + SS_s + SNU_s + SSU_s + REP_s \quad (2)$$

where
$ST_s$≡area overlap of all shots within all target tissue area;
$SN_s$≡area overlap of all shots within all normal tissue area;
$SC_s$≡area overlap of all shots within all critical tissue area;
$SS_s$≡area overlap of all shots within shots;
$SNU_s$≡measure of non-uniformity of shot-normal overlaps;
$SSU_s$≡measure of non-uniformity of shot-shot overlaps; and
$REP_s$≡measure of tight shot cluster formation.

Optimal geometric packing with shot volumes is achieved by minimization of the optimization function which represents the quality of the packing. For purposes of clarity when referring to geometric packing, the volume optimization function will be designated OPTG and the area optimization function will be designated $OPTG_s$.

The shot target overlap on slice s, $ST_s$ and the shot-critical overlap, $SN_s$, for the geometric packing step can be defined calculated as $$ST_s = \sum_{g,t,n} \Big\{ \text{Signed Area}[\text{Overlap}[\text{shot}_{g,s}, \text{target}_{n,t,s}]] - \sum_{g1 > g} \text{Signed Area}[\text{Overlap}[\text{shot}_{g,s}, \text{shot}_{g1,s}, \text{target}_{n,t,s}]] \Big\}$$

$$SC_s = \sum_{g,c,n} \Big\{ \text{Signed Area}[\text{Overlap}[\text{shot}_{g,s}, \text{critical}_{n,c,s}]] - \sum_{g1 > g} \text{Signed Area}[\text{Overlap}[\text{shot}_{g,s}, \text{shot}_{g1,s}, \text{critical}_{n,c,s}]] \Big\}$$

where
s≡an index specifying a slice,
g≡an index specifying a shot,
t≡an index specifying a target structure,
c≡an index specifying a critical structure,
n≡an index specifying a contour of the nested contours of target structure t or critical structure c in slice s,
g1≡an index specifying a shot,
$\text{shot}_{g,s}$≡the contour of shot g on slice s,
$\text{target}_{n,t,s}$≡the $n^{th}$ contour of target t on slice s,
$\text{critical}_{n,c,s}$≡the $n^{th}$ contour of critical structure c on slice s,
Overlap≡a contour circumscribing the overlap of two or more contours, where the contour is counter-clockwise if all the contours have the same orientation (i.e., clockwise or counter-clockwise) and is clockwise otherwise,
Signed Area≡the area circumscribed by either a counter-clockwise contour or the negative area of a clockwise contour.

The area calculation needs to be signed to account for those nested target or critical structure contours which represent "holes" or "dimples" in the structure. For example, if shot and outer target and critical structure contours are counter-clockwise, the nested "holes" are defined to be clockwise. The second term corrects for the shot-shot overlap that has been double counted in the first term.

The calculation of $SN_s$ is found by subtracting the target and critical areas from the shot area, on a shot by shot basis. An example calculation of the shot-shot uniformity term $SNU_s$ is found by squaring the fraction of the shot outside the target.

$$SN_s = \sum_g \Big\{ \text{Area}[\text{shot}_{g,s}] - \sum_{t,n} \text{Signed Area}[\text{Overlap}[\text{shot}_{g,s}, \text{target}_{n,t,s}]] - \sum_{c,n} \text{Signed Area}[\text{Overlap}[\text{shot}_{g,s}, \text{critical}_{n,c,s}]] \Big\}$$

$$SNU_s = \sum_{g,t} \text{Area}[\text{shot}_{g,s}] \left\{ 1 - \frac{\sum_n \text{Signed Area}[\text{Overlap}[\text{shot}_{g,s}, \text{target}_{n,t,s}]]}{\text{Area}[\text{shot}_{g,s}]} \right\}^2$$

where s = an index specifying a slice,
g = an index specifying a shot,
t = an index specifying a target structure,
c = an index specifying a critical structure,
n = an index specifying a contour of the nested contours of target structure t or critical structure c in slice,
$\text{shot}_{g,s}$ = the contour of shot g on slice s,
$\text{target}_{n,t,s}$ = the $n^{th}$ contour of target t on slice s,
$\text{critical}_{n,c,s}$ = the $n^{th}$ contour of critical structure c on slice s,
Overlap = a contour circumscribing the overlap of two or more contours, where the contour is counter-clockwise if all the contours have the same orientation (i.e., clockwise or counter-clockwise) and is clockwise otherwise,
Signed Area = the area circumscribed by either a counter-clockwise contour or the negative area of a clockwise contour,
Area = the area circumscribed by either a clockwise or a counter-clockwise contour (always positive).

If any one shot has a large fraction of the shot-normal overlap, the $SNU_s$ will be significantly larger than the case where the shot-normal overlaps are uniform. Also, the fraction is weighted by the shot contour area because for the same fraction of shot-normal overlap, larger shots produce more overlap.

The calculation of the shot-shot overlap, $SS_s$, and shot-shot overlap uniformity term, $SSU_s$, can be calculated as $$SS_s = \sum_{\substack{g1,g2 \\ g1<g2}} \text{Area}[\text{Overlap}[\text{shot}_{g1,s}, \text{shot}_{g2,s}]]$$

$$SSU_s = \sum_{g1} \frac{1}{\text{Area}[\text{shot}_{g1,s}]} \sum_{\substack{g2 \\ g2>g1}} \{\text{Area}[\text{Overlap}[\text{shot}_{g1,s}, \text{shot}_{g2,s}]]\}^2$$

where s = an index specifying a slice,
$g_1, g_2$ = indices specifying a shot,
$\text{shot}_{g,s}$ = the contour of shot g on slice structure t on slice s,
Overlap = a contour circumscribing the overlap of two or more contours, where the contour is counter-clockwise if all the contours have the same orientation (i.e., clockwise or counter-clockwise) and is clockwise otherwise,
Area = the area circumscribed by either a clockwise or a counter-clockwise contour (always positive).

If only one shot pair has a large function of the shot-shot overlap, $SSU_s$ will be significantly larger than the case where the shot-shot overlaps are uniform.

An example calculation of $REP_s$ can be seen as follows:

$$REP_s = \sum_{g1} \text{Area}[\text{shot}_{g1,s}] \sum_{\substack{g2,g3 \\ g2>g1 \\ g3>g2}} \frac{9}{(f_{g1,g2}^2 + f_{g2,g3}^2 + f_{g3,g1}^2)^3}$$

where s = an index specifying a slice,
$g_1 g_2 g_3$ = indices specifying a shot,
$\text{shot}_{g,s}$ = the contour of shot g on slice s,
Area = the area circumscribed by either a clockwise or a counter-clockwise contour (always positive),
$f_{g1,g2}$ = the fraction of the distance between the current isocenters to that at contact for shots g1 and g2.

If any three shot volumes are all close together, $REP_s$ will contribute to the optimization function. The shots surrounded by other shots (in the bulk of the target) will be affected more than those on the surface. Nonlinear minimization of the optimization function is carried out by using a modified Powell direction set method to deal with the continuous variables (i.e., position and gamma angle). The Powell method is a public domain algorithm and can be found, for example, in Press, William H. et al., *Numerical Recipes in C, The Art of Scientific Computing*, Second Edition, 1992, Cambridge University Press, pages 415-416. Modification of the Powell method includes constraints to insure that only treatable positions and gamma angles are used. Because the number and typical dimensions of the local minima of the optimization function have been found to negate the quadratically convergent nature of the Powell method, it is preferable to use single set of vectors (the basis set) and perform a single minimization along the average direction without basis replacement.

The discrete variables (i.e., aperture size and the number of shots) are optimized using a public domain simulated annealing (combinatorial minimization) approach which can be found, for example, in Press, William H. et al., *Numerical Recipes in C, The Art of Scientific Computing*, Second Edition, 1992, Cambridge University Press, pages 444-455, which has been modified for purposes of this invention. The description of possible system configuration in the annealing algorithm includes the number of shots, and the sizes, positions, gamma angles, and weighting of the shots. Additionally, the options available to the random search generator in the annealing algorithm include adding a shot (up to the maximum number of shots which is pre-defined), removing a shot, increasing the size of a shot, decreasing the size of a shot, and translating a shot. In this way, the scope of the random search in the simulated annealing routine is reduced by directing the random search to regions that are most likely to produce improvement. A well directed search will avoid the heavy computational requirements typical of simulated annealing methods. Alternatively, an artificial intelligence algorithm could be used.

The optimization function is constructed so that its minimization results in high shot-target overlap and low shot-shot and shot critical-overlap. Optionally, a term to penalize a large number of shots can be included. This term can be the number of shots used times a small fraction of the target area in each slice. If an additional shot only adds slightly to the minimization of the optimization function, the addition of the shot is rejected. Within the constraints given, minimization of the optimization function (the Powell method mentioned above is the preferred means to do this minimization) produces the optimal packing of the target volume while sparing critical structures and reducing shot-shot overlap.

Another problem can occur in geometric packing when the distance between slices is comparable to the shot size. The shot volume is being represented by shot contours on the slice set. If the shot size is small compared to the slice separation, the shot is not accurately represented between slices. Therefore it is preferable to add artificial slices interleaved between those of the slice set to improve the representation of the shot volume by shot contours. Alternatively, the use of shot-shot area overlaps can be replaced with the use of shot-shot isocenter separations. This alternative would be more computationally efficient than adding slices.

Note that, because of possible hot spots and interslice misrepresentation of small shots, the geometric packing of individual LGU shots can only be expected to give an approximation to the optimal treatment plan (any procedure that does not rely upon the total three-dimensional dose distribution can only be approximate). However, geometric packing of the individual shot volumes with a proper accounting of hot spots and interslice misrepresentation, can produce a reasonable approximate solution for a treatment plan. This approximate solution is useful as a robust start for the exact method of conforming the treatment volume to the target volume.

For conformation packing, the volume optimization function OPT is the same as for geometric packing. However, for conformation packing, the area optimization function $OPT_s$ is defined as the following equation:

$$OPT_s = -ST_s + SN_s + SC_s + SNU_s \qquad (3)$$

where, $ST_s$=area overlap of all shots within all target tissue area;

$SN_s$=area overlap of all shots within all normal tissue area;

$SC_s$=area overlap of all shots within all critical tissue area; and $SNU_s$=measure of non-uniformity of shot-normal overlap.

For purposes of clarity when referring to conformation packing, the volume optimization function will be designated OPTC and the area optimization function will be designated $OPTC_s$. As with geometric packing, optimal conformation packing is achieved by minimization of the optimization function which represents the quality of the packing. However, rather than packing individual shot volumes, this optimization function uses the three-dimensional dose distribution to conform the overall isodose surface to the surface of the target. The treatment volume is no longer approximated by the set of the individual shot volumes; thus, hot spot and interslice problems are avoided. Instead, the treatment volume is defined by the isodose surface of the three-dimensional dose distribution resulting from all the Gamma Knife shots.

The treatment volume of a non-optimized plan can be very complicated with many holes (e.g., Swiss cheese like), substructures (volumes within holes), and surface ripples. By using the three-dimensional dose distribution resulting from the geometric packing step as an "initialization" for this function, the complexity of the treatment volume is reduced. The intersection of the isodose surface of the overall dose distribution with the slice set determines the dose contours (i.e. the treament volume contours) on the slice set. Specifically, the dose contours are generated using contouring on a two-dimensional dose grid on each slice. The use of "dose" contours rather than "shot" contours introduces the complexity that the dose contours can have complicated shapes. In optimization function calculations, the number of dose contours depends on how many contours the contouring routine finds in the slice. This is in contrast to shot contours where the number depends on how many shots intersect the slice. Otherwise, the terms "shot-target" overlap and "dose-target" overlap are very similar in concept. It will be appreciated that the use of the term "shot" in specifying contour in conformation packing refers to a dose or treatment volume contour, not a shot contour from a single LGU shot as is the case with geometric packing.

The optimization using the isodose surface of the overall dose distribution is similar to the packing of shot volumes except for two important differences. The first difference is that the weighting of the shots is now included in the optimization (the weighting is required to generate the total dose distribution of the shot set). The second is that there are no shot-shot (i.e., dose-dose) overlaps produced in contouring a continuous dose distribution. The optimization function to be minimized depends on the dose-normal and dose-critical volumes as determined by area overlaps (dose-target, dose-critical, and dose-normal area overlaps) on the slice set of the isodose contours of the overall dose distribution with the target and critical structure contours. In addition, the optimization function may also depend on a term which is a measure of the uniformity of the dose-normal overlap to prevent "bulges." The optimization over the continuous shot parameters (i.e., position, gamma angle, and weighting) can be carried out using the modified Powell routine. The discrete shot variables (i.e., shot aperture size and number of shots) can be searched using simulated annealing or intelligent constraint alterations if required. Furthermore, a penalty for large shot numbers will discourage the use of a large number of shots. The optimized plan can be expected to produce isodose contours on the slice set that match the defined target contours, without using an excessive number of shots.

If uniformity of the dose within the target volume is a clinical factor, additional factors must be included in the optimization function to be minimized. Detecting uniformity in the conformation scheme requires tracking of additional isodose surfaces within the treatment volume. If the volumes contained by the additional isodose surfaces are controlled without. significantly altering the conformation of the treatment volume to the target volume, the uniformity of the dose within the target volume will be optimized.

Note also, that in each optimization formula the weighting of the terms can be adjusted to vary the results. For example, the weighting of the term $SC_s$ should be larger than that of the term $SN_s$ to penalize shot-critical overlap more than shot-normal overlap.

A typical method of treatment planning in accordance with the present invention can be seen with reference to FIG. 3A through FIG. 3C. At step 100 an panel of physicians determines that a patient is to be treated by stereotactic radiosurgery. At step 102 a reliable x,y,z coordinate system is fixed relative to the patient by using a conventional stereotactic frame or the like. Using the x,y,z coordinate system established in step 102, at step 104 images of the area of interest in the patient are taken using an imaging system such as computed tomography (CT), magnetic resonance imaging (MRI), angiography, or equivalent other in a going system. At step 106, physicians use the images from step 104 to locate and define the target volume or structure in the patient to be treated, as well as surrounding or critical tissue areas, again using the x,y,z coordinate system previously established.

At step 108 the treatment planner decides whether or not to enter an auto initialization routine in the planning computer. Data is entered into the planning computer through a keyboard or other input device operatively coupled to the planning computer. If the decision is affirmative, at step 110 an initial treatment plan is determined through an automatic packing of the target volume. First, the target volume is divided by the shot size of the collimator to be used with the LGU (there are typically four aperture sizes: 4, 8, 14 and 18 mm) to determine the approximate number of shots. Then, the shots are simply packed into the target volume on a uniform grid to produce an initial treatment plan If auto-initialization is not desired, then an initial treatment plan is manually developed at step 112.

At step 114, the treatment planner decides whether or not to view the results of the initial treatment plan on a video display monitor or the like which is operatively coupled to the planning computer. If the decision is affirmative, at step 116 the planning computer calculates the three-dimensional distribution of the initial treatment plan and displays the isodose contours on the video monitor. At step 118, the treatment planner decides whether or not to modify the initial treatment plan before proceeding. If the decision is affirmative, the treatment planner manually modifies the initial treatment plan at step 120, and the planning computer recalculates the three-dimensional distribution and displays the new isodose curves at step 116. Modification of the plan can continue for as many iterations as desired.

Once the initial treatment plan has been sufficiently modified, or if modification is not desired after step 118, at step 122 the treatment planner decides whether or not to geometrically pack the target volume with individual shot volumes. If the decision is affirmative, at step 124 the planning computer performs the geometric packing. Then, at step 126, the planning computer calculates the three-dimensional dose distribution of the plan and displays the isodose contours on the video display. At step 128, the treatment planner decides whether or not to modify the packing. If the decision is affirmative, the oncologist manually modifies the treatment plan at step 130. The three-dimensional dose distribution of the modified treatment plan is recalculated and the isodose contours are displayed at step 126. Once modification is complete, or if modification is not desired after step 128, at step 132 the treatment planner decides whether or not to repack the shot volumes. If the decision is affirmative, the method continues at step 124.

Once repacking of the shot volumes is complete, or if the treatment planner decides not to perform a geometric packing at all, the process continues at step 134 where the treatment planner decides whether or not to perform a conformation packing of the net treatment volume. If the decision is affirmative, at step 136 the planning computer optimizes the treatment plan by conforming the treatment volume to the target volume.

At step 138, the planning computer then calculates the three-dimensional dose distribution of the plan and displays the isodose contours on the video display. At step 140, the treatment planner decides whether or not to modify the packing. If the decision is affirmative, the treatment planner manually modifies the treatment plan at step 142. The planning computer then recalculates the three-dimensional dose distribution of the modified treatment plan and the new isodose contours are displayed at step 138. Once modification is complete, or if modification is not desired after step 140, at step 144 the treatment planner decides whether or not to reoptimise the treatment plan using conformation parking .If the decision is affirmative, the method continues at step 136.

Once repacking of the treatment plan is complete, or if the treatment planner decides not to perform a conformation packing at all, the process continues at step 146 where the planning computer calculates the three-dimensional dose distribution of the optimal treatment plan and displays the isodose curves on the video display. At step 148 the physicians decide whether or not the plan is acceptable and, if it is, the patient is treated at step 150. Otherwise, the method is repeated at step 152. Note that the treatment planner could repeat the method entirely by starting at the beginning of the process, repeat the geometric packing, repeat the conformation packing, or both, until the desired treatment plan is achieved.

The method of the present invention can be modified to optimize treatment planning for devices other than the Leksell Gamma Knife. For example, where a linear accelerator is used, a "shot volume" would be replaced with the volume resulting from a typical treatment element, such as a five arc configuration. Such a configuration yields a spherical 80% isodose volume, and the packing algorithm could be used to fill the target volume with an appropriate number of the five arc isocenters, in a similar fashion to that described herein for Gamma Knife shots.

Referring to FIG. 4, a stereotactic frame 200 is used to establish an x,y,z coordinate system relative to the patient. Stereotactic frame 200 is used in connection with an imaging system 212 which can be a computed tomography (CT) scanner, magnetic resonance imaging (MRI) scanner, angiography unit or the like, for imaging the target and critical areas. This information is input to a central processing unit 214, which typically includes a processor, memory, disk storage, and video display adapter. Central processing unit 214 also includes means for performing the auto-initialization, geometric packing, conformation packing and related steps described herein, as well as means for calculating the three-dimensional distribution of the treatment plan and displaying the isodose contours. Coupled to central processing unit 214 is a video display 216 or the like, and a user input device 218 such as a keyboard or the like. Additional input and output devices could also be included.

Accordingly, it will be seen that this invention provides for accurate and efficient inverse treatment planning for stereotactic radiosurgery. Although the description above contains many specificities, these should not be construed as limiting the scope of the invention but as merely providing illustrations of some of the presently preferred embodiments of this invention. Thus the scope of this invention should be determined by the appended claims and their legal equivalents.

We claim:

1. A method of optimizing dose delivery for stereotactic radiosurgery, comprising the steps of:
   (a) subjecting a patient to an imaging system to locate and define a target volume of tissue within the patient;
   (b) performing a geometric packing of the target volume with a plurality of radiosurgery shots, each said shot having a shot volume, thereby producing a treatment volume;
   (c) performing a conformation packing of the target volume with the treatment volume to produce an inverse treatment plan; and
   (d) treating the patient with a radiosurgery apparatus according to said inverse treatment plan.

2. A method as recited in claim 1, wherein said step of performing a geometric packing of the target volume includes the step of minimizing a volume optimization function for geometric packing over one or more slices, s, of the target volume, each said slice, s, having a thickness $\Delta_s$, according to $$OPTG = \sum_s \Delta_s OPTG_s$$

where
   OPTG≡the volume optimization function for geometric packing,
   s=an index representing a specific slice,
   $\Delta_s$=the thickness of a slice s,
   $OPTG_s$≡an area optimization function for geometric packing calculated on slice s according to the equation $$OPTG_s = -ST_s + SN_s + SC_s + SS_s + SNU_s + SSU_s + REP_s$$

where
   $ST_s$=area overlap of shots within said target volume,
   $SN_s$=area overlap of shots within normal tissue,
   $SC_s$=area overlap of shots within critical tissue,
   $SS_s$=area overlap of shots within shots,
   $SNU_s$=a measure of non-uniformity of shot-normal overlaps,
   $SSU_s$=a measure of non-uniformity of shot-shot overlaps, and
   $REP_s$=a measure of tight shot cluster formation.

3. A method as recited in claim 2, wherein said step of performing a conformation packing of the target volume includes the step of minimizing a volume optimization function for conformation packing over one or more slices, s, of the target volume, each said slice, s, having a thickness $\Delta_s$, according to $$OPTC = \sum_s \Delta_s OPTC_s$$

where
   OPTC≡the volume optimization function for conformation packing,
   s=an index representing a specific slice,
   $\Delta$=the thickness of a slice s,
   $OPTC_s$an area optimization function for conformation packing calculated on slice s according to the equation $$OPTC_s = -ST_s + SN_s + SC_s + SNU_s$$

where
   $ST_s$=area overlap of shots within said target volume,
   $SN_s$=area overlap of shots within normal tissue,
   $SC_s$=area overlap of shots within critical tissue, and
   $SNU_s$=a measure of non-uniformity of shot-normal overlaps.

4. A method as recited in claim 3, further comprising the step of preparing an initial treatment plan prior to said step of performing a geometrical packing of the target volume.

5. A method of optimizing dose delivery for stereotactic radiosurgery, comprising the steps of:
   (a) establishing an x,y,z coordinate system relative to a patient to be treated;
   (b) subjecting the patient to an imaging system to locate and define a target volume of tissue within the patient relative to said x,y,z coordinate system;
   (c) performing a geometric packing of the target volume with a plurality of radiosurgery shots by minimizing a first optimization function, each said shot having a shot volume, thereby producing a treatment volume;
   (d) performing a conformation packing of the target volume with the treatment volume by minimizing a second optimization function to produce an inverse treatment plan; and
   (e) treating the patient with a radiosurgery apparatus according to said inverse treatment plan.

6. A method as recited in claim 5, wherein said first optimization function is minimized according to $$OPTG = \sum_s \Delta_s OPTG_s$$

where
   OPTG≡the volume optimization function for geometric packing,
   s=an index representing a specific slice,
   $\Delta_s$=the thickness of a slice s,
   $OPTG_s$≡an area optimization function for geometric packing calculated on slice s according to the equation $$OPTG_s = -ST_s + SN_s + SC_s + SS_s + SNU_s + SSU_s + REP_s$$

where
   $ST_s$=area overlap of shots within said target volume,
   $SN_s$=area overlap of shots within normal tissue,
   $SC_s$=area overlap of shots within critical tissue,
   $SS_s$=area overlap of shots within shots,
   $SNU_s$=a measure of non-uniformity of shot-normal overlaps,
   $SSU_s$=a measure of non-uniformity of shot-shot overlaps, and
   $REP_s$=a measure of tight shot cluster formation.

7. A method as recited in claim 6, wherein said second optimization function is minimized according to $$OPTC = \sum_s \Delta_s OPTC_s$$

where
   OPTC≡the volume optimization function for conformation packing,
   s=an index representing a specific slice,
   $\Delta_s$=the thickness of a slice s, $OPTC_s = an$ area optimization function for conformation packing calculated on slice s according to the equation $$OPTC_s = -ST_s + SN_s + SC_s + SNU_s$$

where
- $ST_s$=area overlap of shots within said target volume,
- $SN_s$=area overlap of shots within normal tissue,
- $SC_s$=area overlap of shots within critical tissue, and
- $SNU_s$=a measure of non-uniformity of shot-normal overlaps.

8. A method for treating a patient with an optimized stereotactic radiosurgery treatment plan, comprising the steps of:

(a) establishing an x,y,z coordinate system relative to a patient;
   (b) subjecting the patient to an imaging system to locate and define a target volume of tissue within the patient relative to said x,y,z coordinate system;
   (c) performing a geometric packing of the target volume with a plurality of radiosurgery shots by minimizing a first optimization function, each said shot having a shot volume, thereby producing a first treatment plan having treatment volume;
   (d) calculating a three-dimensional dose distribution for said first treatment plan and displaying isodose curves for said first treatment plan on a video display device;
   (e) performing a conformation packing of the target volume with the treatment volume by minimizing a second optimization function to produce a second treatment plan;
   (f) calculating a three-dimensional dose distribution for said second treatment plan and displaying isodose curves for said second treatment plan on a video display device; and
   (g) radiating the patient with a radiosurgery apparatus according to said second treatment plan.

9. A method as recited in claim 8, wherein said first optimization function is minimized according to $$OPTG = \sum_s \Delta_s OPTG_s$$

where
- OPTG=the volume optimization function for geometric packing,
- s=an index representing a specific slice,
- $\Delta_s$=the thickness of a slice s,
- $OPTG_s$=an area optimization function for geometric packing calculated on slice s according to the equation $$OPTG_s = -ST_s + SN_s + SC_s + SS_s + SNU_s + SSU_s + REP_s$$

where
- $ST_s$=area overlap of shots within said target volume,
- $SN_s$=area overlap of shots within normal tissue,
- $SC_s$=area overlap of shots within critical tissue,
- $SS_s$=area overlap of shots within shots,
- $SNU_s$=a measure of non-uniformity of shot-normal overlaps, $SSU_s$=a measure of non-uniformity of shot-shot overlaps, and
- $REP_s$=a measure of tight shot cluster formation.

10. A method as recited in claim 9, wherein said second optimization function is minimized according to $$OPTC = \sum_s \Delta_s OPTC_s$$

where
- OPTC=the volume optimization function for conformation packing,
- s=an index representing a specific slice,
- $\Delta_s$=the thickness of a slice s,
- $OPTC_s$=an area optimization function for conformation packing calculated on slice s according to the equation $$OPTC_s = -ST_s + SN_s + SC_s + SNU_s$$

where
- $ST_s$=area overlap of shots within said target volume,
- $SN_s$=area overlap of shots within normal tissue,
- $SC_s$=area overlap of shots within critical tissue, and
- $SNU_s$=a measure of non-uniformity of shot-normal overlaps.

11. An apparatus for optimizing dose delivery for stereotactic radiosurgery, comprising:

(a) a stereotactic frame;
   (b) an imaging system;
   (c) means for performing a geometric packing of a target volume of tissue with one or more radiosurgery shots and producing a treatment volume, each said shot having a shot volume, said target volume located and defined from said imaging system and said stereotactic frame; and
   (d) means for performing a conformation packing of the target volume with the treatment volume to produce an inverse treatment plan.

12. An apparatus as recited in claim 11, further comprising:

(a) means for minimizing a first optimization function over one or more slices, s, of the target volume, each said slice, s, having a thickness $\Delta_s$, according to the equation $$OPTG = \sum_s \Delta_s OPTG_s$$

where
- OPTG=the volume optimization function for geometric packing,
- s=an index representing a specific slice,
- $\Delta_s$=the thickness of a slice s,
- $OPTG_s$=an area optimization function for geometric packing calculated on slice s according to the equation $$OPTG_s = -ST_s + SN_s + SC_s + SS_s + SNU_s + SSU_s + REP_s$$

where
- $ST_s$=area overlap of shots within said target volume,
- $SN_s$=area overlap of shots within normal tissue,
- $SC_s$=area overlap of shots within critical tissue,
- $SS_s$=area overlap of shots within shots,
- $SNU_s$=a measure of non-uniformity of shot-normal overlaps,
- $SSU_s$=a measure of non-uniformity of shot-shot overlaps, and
- $REP_s$=a measure of tight shot cluster formation; and (b) means for minimizing a second volume optimization function over one or more slices, s, of the target volume, each said slice, s, having a thickness $\Delta_s$, according to the equation $$OPTC = \sum_s \Delta_s OPTC_s$$

where
OPTC≡the volume optimization function for conformation packing,
s≡an index representing a specific slice,
$\Delta_s$≡the thickness of a slice s,
$OPTC_s$≡an area optimization function for conformation packing calculated on slice s according to the equation $$OPTC_s = -ST_s + SN_s + SC_s + SNU_s$$

where
$ST_s$≡area overlap of shots within said target volume,
$SN_s$≡area overlap of shots within normal tissue,
$SC_s$≡area overlap of shots within critical tissue, and $SNU_s$≡a measure of non-uniformity of shot-normal overlaps.

13. A method of optimizing dose delivery for stereotactic radiosurgery, comprising the steps of:
(a) subjecting a patient to an imaging system to locate and define a target volume of tissue within the patient;
(b) preparing an initial treatment plan;
(c) performing a geometric packing of the target volume with a plurality of radiosurgery shots, each said shot having a shot volume, thereby producing a treatment volume;
(d) said step of performing a geometric packing of the target volume including the step of minimizing a volume optimization function for geometric packing over one or more slices, s, of the target volume, each said slice, s, having a thickness $\Delta_s$, according to $$OPTG = \sum_s \Delta_s OPTG_s$$

where
OPTG≡the volume optimization function for geometric packing,
s≡an index representing a specific slice, $\Delta_s$≡the thickness of a slice s, $OPTG_s$≡an area optimization function for geometric packing calculated on slice s according to $$OPTG_s = -ST_s + SN_s + SC_s + SS_s + SNU_s + SSU_s + -REP_s$$

where
$ST_s$≡area overlap of shots within said target volume,
$SN_s$≡area overlap of shots within normal tissue,
$SC_s$≡area overlap of shots within critical tissue,
$SS_s$≡area overlap of shots within shots,
$SNU_s$≡a measure of non-uniformity of shot-normal overlaps,
$SSU_s$≡a measure of non-uniformity of shot-shot overlaps, and $REP_s$≡a measure of tight shot cluster formation;
(e) performing a conformation packing of the target volume with the treatment volume to produce an inverse treatment plan;
(f) said step of performing a conformation packing of the target volume including the step of minimizing a volume optimization function for conformation packing over one or more slices, s, of the target volume, each said slice, s, having a thickness $\Delta_s$, according to the equation $$OPTC = \sum_s \Delta_s OPTC_s$$

where
OPTC≡the volume optimization function for conformation packing,
s≡an index representing a specific slice,
$\Delta_s$≡the thickness of a slice s,
$OPTC_s$≡an area optimization function for conformation packing calculated on slice s according to $$OPTC_s = -ST_s + SN_s + SC_s + SNU_s$$

where
$ST_s$≡area overlap of shots within said target volume,
$SN_s$≡area overlap of shots within normal tissue,
$SC_s$≡area overlap of shots within critical tissue, and
$SNU_s$≡a measure of non-uniformity of shot-normal overlaps; and
(g) treating said patient with a radiosurgery apparatus according to said inverse treatment plan.

14. A method of optimizing dose delivery for stereotactic radiosurgery, comprising the steps of:
(a) establishing an x,y,z coordinate system relative to a patient to be treated;
(b) subjecting the patient to an imaging system to locate and define a target volume of tissue within the patient relative to said x,y,z coordinate system;
(c) performing a geometric packing of the target volume with a plurality of radiosurgery shots by minimizing a first optimization function according to $$OPTG = \sum_s \Delta_s OPTG_s$$

where
OPTG≡the volume optimization function for geometric packing,
s≡an index representing a specific slice,
$\Delta_s$≡the thickness of a slice s,
$OPTG_s$≡an area optimization function for geometric packing calculated on slice s according to $$OPTG_s = -ST_s + SN_s + SC_s + SS_s + SNU_s + SSU_s + -REP_s$$

where
$ST_s$≡area overlap of shots within said target volume,
$SN_s$≡area overlap of shots within normal tissue,
$SC_s$≡area overlap of shots within critical tissue,
$SS_s$≡area overlap of shots within shots, $SNU_s \equiv$ a measure of non-uniformity of shot-normal overlaps, $SSU_s \equiv$ a measure of non-uniformity of shot-shot overlaps, and $REP_s \equiv$ a measure of tight shot cluster formation, each said shot having a shot volume, thereby producing a treatment volume;

(d) performing a conformation packing of the target volume with the treatment volume by minimizing a second optimization according to $$OPTC = \sum_s \Delta_s OPTC_s$$

where

OPTC = the volume optimization function for conformation packing, $s =$ an index representing a specific slice, $\Delta_s =$ the thickness of a slice s, $OPTC_s =$ an area optimization function for conformation packing calculated on slice s according to $$OPTC_s = -ST_s + SN_s + SC_s + SNU_s$$

where $ST_s =$ area overlap of shots within said target volume, $SN_s =$ area overlap of shots within normal tissue, $SC_s =$ area overlap of shots within critical tissue, and $SNU_s \equiv$ a measure of non-uniformity of shot-normal overlaps, to produce an inverse treatment plan; and (e) treating the patient with a radiosurgery apparatus according to said inverse treatment plan.

* * * * *